(12) United States Patent
Park et al.

(10) Patent No.: US 9,072,592 B2
(45) Date of Patent: Jul. 7, 2015

(54) METHODS FOR PRODUCING AND USING SILK NANOFIBER NERVE CONDUITS

(75) Inventors: Young Hwan Park, Seoul (KR); Chang Seok Ki, Gyeonggi-do (KR); Hyun Jeung Kim, Seoul (KR); Sook Young Park, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 688 days.

(21) Appl. No.: 13/389,787

(22) PCT Filed: Aug. 11, 2010

(86) PCT No.: PCT/KR2010/005280
§ 371 (c)(1),
(2), (4) Date: Feb. 27, 2012

(87) PCT Pub. No.: WO2011/019211
PCT Pub. Date: Feb. 17, 2011

(65) Prior Publication Data
US 2012/0150205 A1    Jun. 14, 2012

(30) Foreign Application Priority Data

Aug. 12, 2009   (KR) .................. 10-2009-0074161

(51) Int. Cl.

| | |
|---|---|
| *D01D 5/06* | (2006.01) |
| *A61F 2/04* | (2013.01) |
| *D01D 1/02* | (2006.01) |
| *D01D 1/06* | (2006.01) |
| *D01D 5/00* | (2006.01) |
| *D01F 4/02* | (2006.01) |
| *A61L 27/36* | (2006.01) |
| *A61L 27/56* | (2006.01) |

(52) U.S. Cl.
CPC .. *A61F 2/04* (2013.01); *D01D 1/02* (2013.01); *D01D 1/06* (2013.01); *D01D 5/003* (2013.01); *D01D 5/0046* (2013.01); *D01D 5/0076* (2013.01); *D01F 4/02* (2013.01); *A61L 27/3604* (2013.01); *A61L 27/56* (2013.01); *A61L 2400/12* (2013.01); *A61L 2430/32* (2013.01)

(58) Field of Classification Search
CPC ..... D01D 1/106; D01D 5/003; D01D 5/0046; D01D 5/06; D01D 1/02; D01F 4/02
USPC ........... 264/10, 169, 202, 213, 334, 338, 464, 264/465, 466, 484
See application file for complete search history.

(56) References Cited

U.S. PATENT DOCUMENTS

| | | | | |
|---|---|---|---|---|
| 1,818,549 | A  * | 8/1931 | Furman ........................ | 264/169 |
| 4,808,324 | A  * | 2/1989 | Periard et al. ................ | 508/115 |
| 2003/0100108 | A1 | 5/2003 | Altman et al. | |
| 2003/0155670 | A1 * | 8/2003 | O'Brien .................... | 264/202 X |
| 2004/0110439 | A1 * | 6/2004 | Chaikof et al. .............. | 442/123 |
| 2009/0318963 | A1 * | 12/2009 | Asakura .................... | 264/202 X |
| 2011/0287082 | A1 * | 11/2011 | Smith et al. .................. | 424/444 |

FOREIGN PATENT DOCUMENTS

| | | |
|---|---|---|
| KP | 1020080049095 | 6/2008 |
| KR | 10-0718073 | 5/2007 |
| KR | 1020090041271 | 4/2009 |
| WO | WO-2008004356 A1 * | 1/2008 |

OTHER PUBLICATIONS

A.C. Lee et al., Controlled release of nerve growth factor enhances sciatic nerve regeneration, Exp. Neurol., 184, 295-303, 2003.
B. Schlosshauer et al., "Rat Schwann cells in bioresorbable nerve guides to promote and accelerate axonal regeneration," Brain Res., 963,321-326, 2003.
Aldini et al. (1996), "Effectiveness of a bioabsorbable conduit in the repair of peripheral nerves," Biomaterials, vol. 17, No. 10, pp. 959-962.
International Search Report for PCT/KR2010/005280, mailed Apr. 26, 2011.

* cited by examiner

*Primary Examiner* — Leo B Tentoni
(74) *Attorney, Agent, or Firm* — Lathrop & Gage LLP

(57) ABSTRACT

The present invention relates to a silk nanofiber nerve conduit characterized in that fibroin nanofibers having a diameter of 200 to 400 nm, originated from silk fiber, are stacked layer upon layer to form a porous conduit-shape; and a method for producing thereof, more specifically, to a method for producing a silk nanofiber nerve conduit comprising: (Step 1) preparing a fibrous spinning solution; (Step 2) producing a silk nanofiber of conduit-shape by electrospinning the fibrous spinning solution prepared in step 1 into the cylindrical collecting part coated with polyethyleneoxide; and (Step 3) separating a silk nanofiber of conduit-shape produced in step 2 from the collecting part. The silk nanofiber nerve conduit of the present invention has excellent biocompatibility; allows the body fluid to be exchanged inter in and out of conduit through pores of the conduit, as well; has a proper elasticity, tensile strength, and tear strength. Due to these properties, the silk nanofiber nerve conduit of the present invention helps the regeneration of the nerve injury to recover a motor skill and a sensory function, and thus shows an excellent effect of nerve regeneration. Therefore, the silk nanofiber nerve conduit of the present invention can be used in treating a nerve injury instead of an existing synthetic polymeric nerve conduit.

4 Claims, 4 Drawing Sheets

Figure 1:
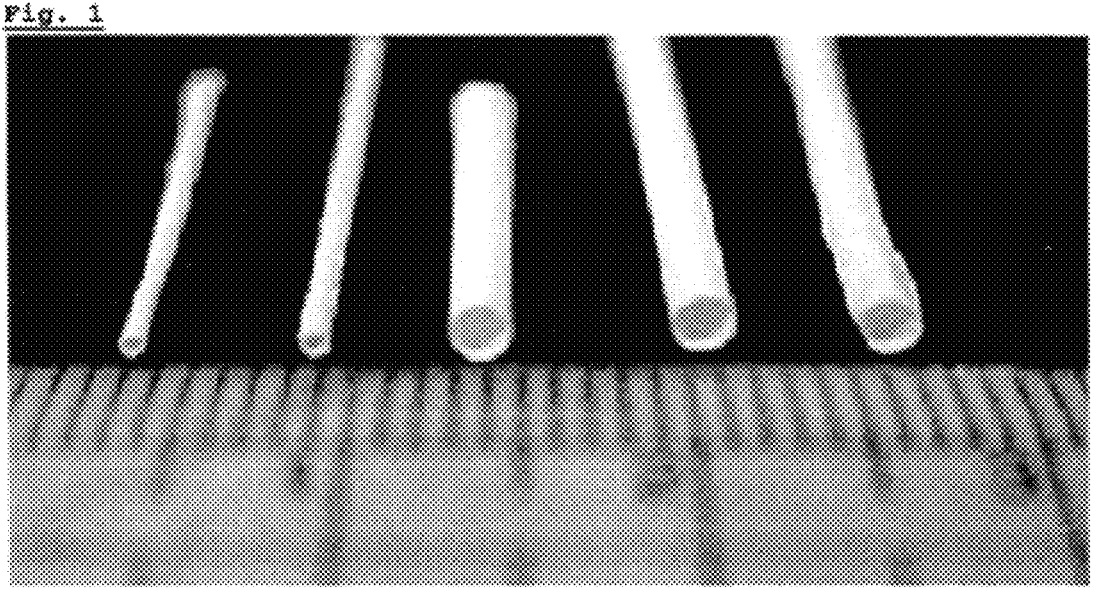

Fig. 2
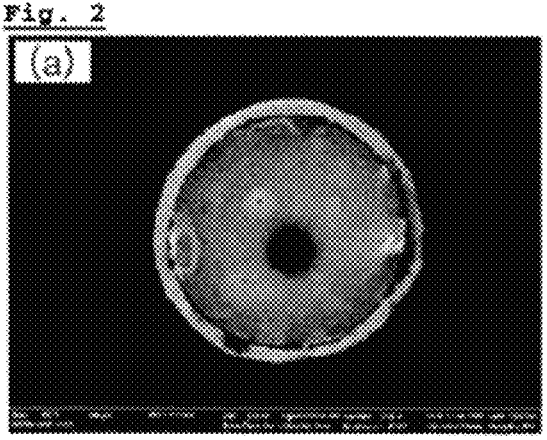
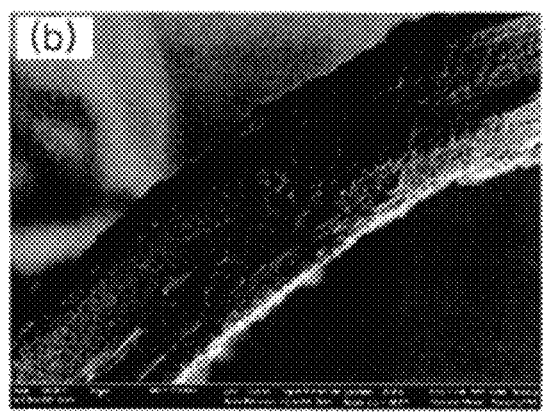
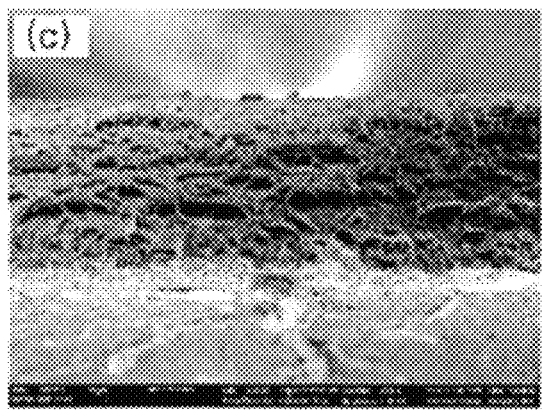
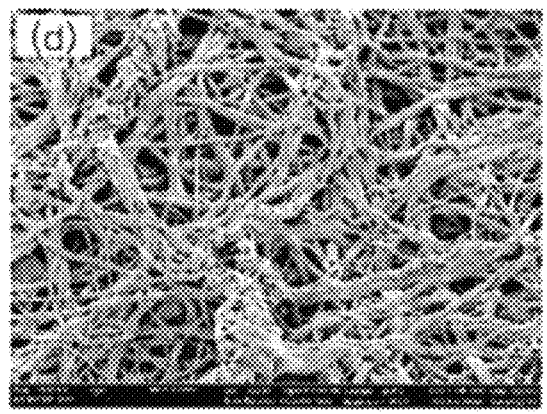

METHODS FOR PRODUCING AND USING SILK NANOFIBER NERVE CONDUITS

CROSS-REFERENCE TO RELATED APPLICATIONS

This application is a U.S. National Stage Application under 35 U.S.C. §371 of International Application No. PCT/KR2010/005280, filed Aug. 11, 2010, which claims the benefit of Korean Application No. 10-2009-0074161, filed Aug. 12, 2009. Both of these applications are hereby incorporated by reference in their entireties.

TECHNICAL FIELD

The present invention relates to a silk nanofiber nerve conduit characterized in that fibroin nanofibers having a diameter of 200-400 nm, originated from silk fiber, are stacked layer upon layer to form a porous conduit-shape and a method for producing thereof.

BACKGROUND ART

Injury of nerve tissue is mainly caused by car accidents emerged from the development of the transportation, cancer according to the environmental pollution and side effects of the operations related to nerve system (B. Schlosshauer et al., "Rat Schwann cells inbioresorbable nerve guides to promote and accelerate axonal regeneration," Brain Res., 963, 321-326, 2003). The injury of nerve tissue results in incapacity of a motor skill and sensory paralysis of the muscle which used to be controlled by the injured nerve.

In order to treat the symptom of nerve injury, a method connecting severed nerve to nerve and a method connecting injured tissue to a normal nerve obtained from the body part which is hardly used or less important have been mainly used. Regarding these methods, the method connecting nerve to nerve directly can be only applied to the nerve tissue having minor injury or very short length. This method cannot be applied to the specific length of nerve which is often treated in the practical operations. For the method autografting normal nerve tissue obtained from the body part to the injured nerve tissue, another nerve injury can be occurred in the body part from which the normal nerve tissue was removed. Also, this method has difficulty for fitting the thickness and shape of the autografted nerve tissue into those of the injured nerve tissue. According to the clinical results which are reported in connection with these methods, five years later from when these methods were used, the patients' capacity for a motor skill was recovered 25% and the sensory function was recovered only 1-3%. In this regard, the usefulness of these methods is not trustworthy. (A. C. Lee et al., "Controlled release of nerve growth factor enhances sciatic nerve regeneration," Exp. Neurol., 184, 295-303, 2003). Recently, in order to replace these methods, a lot of researches have been studied with respect to injured nerve and nerve conduit which helps nerves to perform normal nerve function.

A nerve conduit is a tube inducing nerve connection to the inside of an artificial tube to which the tip of severed nerves is fixed. The method for using the nerve conduit has some advantages. First, the method can block penetration of scar tissue which disturbs nerve generation from the environment. Second, the method can lead the growth of neuraxis (an essential constituent of nerve for communication) to appropriate direction. Last, the method can help regeneration accelerator substances which are secreted from nerve itself to be inside of the tube, while the substances which disturb nerve generation are blocked from the outside.

For the materials of nerve conduit, body tissues (e.g., vein, epineurium, muscle tissue removed of cell, etc.), natural polymers (e.g., collagen, chitosan, etc.), synthetic polymers (e.g., silicon, polylactic acid (PLA), polyglycolic acid (PGA), polylactic acid-co-glycolic acid (PLGA), polycaprolactone, poly lactic acid-co-caprolactone, poly hydroxybutyric acid-co-hydroxyvaleric acid, poly phosphoester, etc.) have been mainly researched. However, if body tissues are used as the materials of nerve conduit, the supply of the tissues are not enough and if body tissues are not obtained by autograft, the usage of nerve conduit is limited due to an immune reaction. Also, if natural polymers are used, the polymers are easily absorbed in the body and the properties are hard to control. Accordingly, natural polymers have many unsolved problems to be used as a material of nerve conduit. Recently, synthetic polymers which have a plurality of supply chains and excellent properties have been primarily studied as the materials for the nerve conduit.

For nerve conduit, it is essential to meet the following requirements. First, inner space of nerve conduit has to be maintained during regeneration and restoration of nerve tissue. Second, nerve conduit has to have proper elasticity and tensile strength in order to keep the sutures of nerve endings stable with the movement of the surgical region. Third, nerve conduit has to be biodegradable according to the regeneration stage of the nerve tissue in order to reduce additional removal procedure. Fourth, tissue rejection against nerve conduit has to be avoided or minimized. Fifth, nerve conduit does not have infectious factors such as virus or bacteria, etc. Sixth, nerve conduit needs to have proper permeability to exchange body fluid in and out of nerve conduit. Seventh, breakdown products of nerve conduit need to have non-toxic properties.

In clinics, non-degradable silicon tube is commonly used, but since this tube is remained in the body even though nerves are regenerated, it causes disadvantages such as chronic inflammation, calcium products of silicon tube and several pains originated from the pressed regenerated nerves; therefore, use thereof has been gradually decreasing. Recently, nerve conduit comprising biodegradable polymers, which melt in the body, has been developed and applied in clinics (e.g., Neurotuve-® by Neuroregen, LLC, USA). This is made of polyglycolic acid (PGA) which is typically used as surgical suture and developed for restoration of isolated sensory nerve within 3 cm of length. The outside of this product has been reformed to a woven structure to maintain inner shape of the product against bending.

Meanwhile, a nerve conduit comprising the same PGA has been developed in Japan for longer isolated nerves, wherein inside of the nerve conduit is filled with collagen sponge which has high-tissue affinity and outside of the nerve conduit is coated with collagen solution several times. As a result of animal testing regarding this nerve conduit, it was confirmed that the isolated peripheral nerve which was 8 cm length was perfectly restored, and the nerve conduit has been used in clinic since 2002 (Korean Registered Patent No. 10-0718073).

Among the currently available nerve conduits in the market, although a collagen-based nerve conduit has excellent biodegradability, the nerve conduit has following problems. Preparation and storage of the collagen is complicate since the collagen of the nerve conduit has to be extracted from animals. Producing large quantity of the collagen is not suitable and the cost of the nerve conduit is very expensive. These disadvantages limit utilizing the nerve conduit in clinics. In addition, the collagen-based nerve conduit has fast velocity of dissolution in the body; causes immune reaction and infectious disease; and has weak tensile strength in the body. For the synthetic polymer nerve conduit such as polylactic acid (PLA), polylactic acid-co-glycolic acid (PLGA), etc., which was proved its biocompatibility, although the nerve conduit has excellent structure safety and tensile strength, due to polymer tubular shape thereof, the body fluid can not be easily exchangeable and inflammation can be occurred because the biodegradation period is longer than 2 years and the breakdown products are acidic.

In this regard, the inventors of the present invention have researched a new kind of nerve conduit which can be used as a replacement of the existing synthetic polymers nerve conduit and found that silk nano-fiber nerve conduit has excellent biocompatibility, allows the body fluid to be exchanged in and out of the conduit through pores of the conduit, and has a proper elasticity, tensile strength and tear strength. Also, since the nerve conduit remarkably regenerates injured nerves to recover a motor skill and sensory function of the injured nerves, the inventors concluded that silk nano-fiber nerve conduit can be used to treat injured nerves as a replacement of the existing synthetic polymers nerve conduit and completed the present invention.

DISCLOSURE

Technical Problem

The present invention aims to provide silk nano-fiber nerve conduit having excellent biocompatibility and showing remarkable nerve regeneration effect, and method for producing thereof.

Technical Solution

In order to achieve the object explained above, the present invention provides silk nano-fiber nerve conduct characterized in that fibroin nano-fibers having a diameter of 200-400 nm, originated from silk fibers, are stacked layer upon layer to form a porous conduit-shape.

Further, the present invention provides a method for producing a silk nanofiber nerve conduit comprising steps of: preparing a fibrous spinning solution (Step 1); producing a silk nanofiber of conduit-shape by electrospinning the fibrous spinning solution prepared in step 1 into the cylindrical collecting part coated with polyethyleneoxide (Step 2); and separating a silk nanofiber of conduit-shape produced in step 2 from the collecting part (Step 3).

Advantageous Effects

Silk nanofiber nerve conduit of the present invention has excellent biocompatibility; allows the body fluid to be exchanged in and out of conduit through pores of the conduit; and has a proper elasticity, tensile strength, and tear strength. Due to these properties, the silk nanofiber nerve conduit of the present invention helps the regeneration of the nerve injury to recover a motor skill and a sensory function, and shows an excellent effect of nerve regeneration. Therefore, the silk nanofiber nerve conduit of the present invention may be used in treating a nerve injury as a replacement of an existing synthetic polymeric nerve conduit.

BRIEF DESCRIPTIONS OF DRAWINGS

Figure 3:
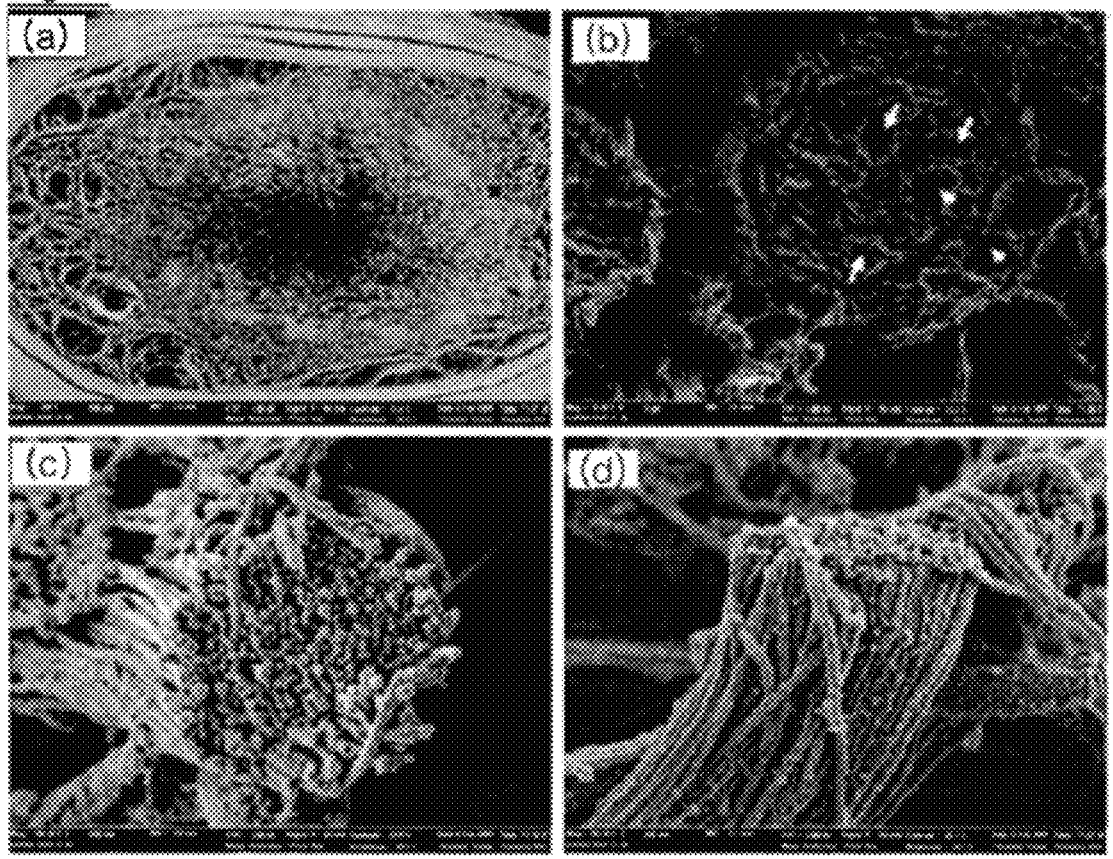
Figure 4:
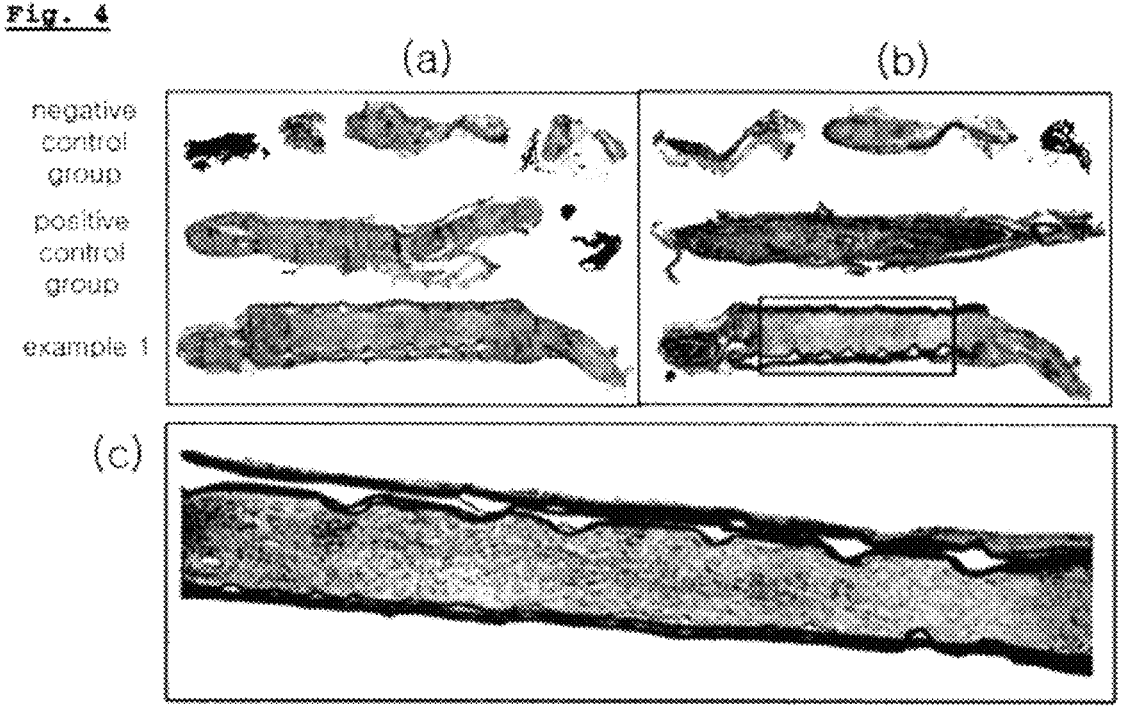

FIG. 1 presents an image of silk nanofiber nerve conduit according to the present invention;

FIG. 2 presents electro-microscopic images of silk nanofiber nerve conduit according to the present invention, in which ((a) is a cross-section image, (b) is a ×100 magnified cross-section image, (c) is a ×1000 magnified cross-section image, and (d) is a fiber structure of silk nanofiber nerve conduit surface);

FIG. 3 presents electro-microscopic images of inside of the nerve conduit after 10 weeks from when silk nanofiber nerve conduit was autografted into mouse, in which ((a) is inside of the nerve conduit, (b) is an magnified image of (a) in which an arrow indicates regenerated nerve bundle, (c) is an image magnified the cross section of regenerated nerve bundle indicated by an arrow in (b), (d) is an image magnified the side of regenerated nerve bundle indicated by an arrow in (b)); and FIG. 4 presents a histological analyzed image of inside of the nerve conduit after 10 weeks from when silk nanofiber nerve conduit was autografted into mouse acquired by ((a) hematoxylin-eosin staining as basic staining, (b) Luxol fast blue staining image specifically staining nerve bundle, and (c) is an image magnified Example 1 of (b) in which the blue line in the conduit indicates regenerated nerve bundle).

BEST MODE

The present invention provides a silk nanofiber nerve conduit characterized in that fibroin nanofibers having a diameter of 200-400 nm, originated from silk fiber, are stacked layer upon layer to form a porous conduit-shape.

Hereinafter, the present invention will be explained in greater detail.

The silk nanofiber is made from the fiber from the reeled-off cocoon which is grown by mulberry. The silk nanofiber has been used as a high-quality fiber material for the past decades because of its high-tensile strength, glossiness, excellent dyeing properties, etc. Also, the silk fiber has a structure in which two threads of fibroin are covered with the external membrane of sericin. The fibroin has excellent bio-affinity and does not affect any other tissues around it. Accordingly, the fibroin may be variously used for food, medicine, medical supplies, etc., in various forms including powder, gel aqueous solution, etc.

The thickness of the silk nanofiber nerve conduit is preferably 0.1 to 0.3 mm. If the thickness is less than 0.1 mm, inside of nerve conduit is pressed under external pressure during surgical procedures and if the thickness is more than 0.3 mm, the bending elasticity is decreased.

In cross section, the silk nanofiber nerve conduit may preferably have a structure in which fine fibers are stacked layer upon layer and the silk nanofibers having a diameter of approximately 200 to 400 nm are irregularly intertwined, forming pores therein. Through pores, the body fluid may be exchanged in and out of conduit and the limitation of the existing synthetic polymer nerve conduit has been overcome, wherein the body fluid can not be exchanged in and out of the conduit since there are no pores.

The size of the formed pores is preferably 50 to 250 μm. If the size is less than 50 μm, the size of pores is too small to exchange the body fluid in and out of the conduit and if the size is more than 250 μm, regeneration accelerator substances formed inside of the conduit are leaked and scar tissue of the outside of conduit is passed through.

The silk nanofiber nerve conduit may preferably have sufficient elasticity, tensile strength and tear strength to connect severed nerve to nerve with surgical suture under wet condition.

In addition, the present invention provides producing method of the silk nanofiber nerve conduit.

The present invention provides a method for producing a silk nanofiber nerve conduit, including steps of: preparing a fibrous spinning solution (Step 1); producing a silk nanofiber of conduit-shape by electrospinning the fibrous spinning solution prepared in step 1 into the cylindrical collecting part coated with polyethyleneoxide (PEO) (Step 2); and separating a silk nanofiber of conduit-shape produced in step 2 from the collecting part (Step 3).

Each step will be explained in greater detail below.

First of all, step 1 of the present invention prepares fibrous spinning solution. The fibrous spinning solution may be prepared by: removing sericin from the silk fiber (Step a); preparing silk fibroin solution by washing, drying, and dialyzing silk fiber from which sericin is removed (Step b); preparing silk fibroin sponge by lyophilizing the silk fibroin solution (Step c); and filtering the silk fibroin sponge after dissolving in designated solvent (Step d).

The silk fiber has a structure in which two threads of fibroin are covered by the external membrane of sericin. Since the fibroin has excellent bioaffinity and does not affect any body tissues, the fibroin may be fabricated into various forms such as powder, gel aqueous solution, etc. and diversely used in forms of food, medicine, medical supplies, etc. If the spinning solution is prepared with the silk fiber, sericin is preferably removed from the silk fiber to maximize biocompatibility. Sericin may be removed by submerging silk fiber in sodium oleate, sodium carbonate solution and heating the same.

The silk fibroin solution may be produced by: repeatedly washing sericin-removed silk nanofiber with distilled water, drying, dissolving in the mixed solution of calcium chloride, water and ethanol, placing in dialyzing diaphragm, and dialyzing with distilled water. The dialyzing diaphragm may preferably have 12 to 14 kDa of MWCO. With the silk fibroin solution, silk fibrous spinning solution may be produced by lyophilizing the silk fibroin solution, preparing silk fibroin sponge, dissolving the sponge in formic acid, and filtering the product.

For the fibrous spinning solution, 12 to 18% concentration is preferable for the efficient spinning process and to obtain regular form of fiber. Within the concentration from 12 to 18%, when the concentration is increased, the thickness of the fiber is increased. If the concentration is less than 12%, the content of the silk in the spinning solution becomes too low to form a fiber, and if the concentration is more than 18%, the viscosity of the solution becomes too high to form a fiber with electricity, therefore, stable electro-spinning may not be continued.

In step 2, a silk nanofiber of conduit-shape is prepared by electro-spinning the fibrous spinning solution prepared in step 1 into the cylindrical collecting part coated with polyethyleneoxide (PEO).

The cylindrical collecting part coated with PEO may preferably be a metallic rod coated with 5 to 15% of PEO. If the metallic rod is coated less than 5% of PEO, the coating may not be uniformly formed over the entire surface of the rod. If the metallic rod is coated more than 15% of PEO, PEO layers may become too thick.

A silk nanofiber of conduit-shape may be prepared by placing the fibrous spinning solution prepared in step 1 in a sealed container such as syringe and releasing with a regular speed by using controlled volume pump. At this time, it is preferable to use tubular spinneret made of metal such as a needle of syringe.

The electro-spinning may be performed by using electro-spinning device which may include power supply device, electrode, spinneret, ground contact part, spinning solution delivery part and collecting part. The electro-spinning device operates to apply voltage such as direct current (DC) voltage, wherein the range of the voltage is preferably between 5 and 20 kV. The electrode is connected from output part of the power supply device to the spinneret (i.e., the needle of syringe). If metallic conduit is used as releasing part, the metallic conduit may also work as electrodes. The ground part may include two parts, that is, the ground for preventing malfunction caused by leaking high voltage of control volume pump which controls the volume of the spinning solution, and the ground of the collecting part. For the collecting part, a circular metallic rod made of stainless steel may be used to prepare tubular structure, and the metallic rods with various diameters may be used depending on the desirable inner diameter of the conduit. The collecting part may preferably spin at 100 to 300 rpm to spread nanofiber on the surface uniformly while electro-spinning is processed.

In step 3, the silk nanofilber having conduit-shape produced in step 2 is sperated from the collecting part.

After electro-spinning in step 2, the collecting part may be submerged in methanol or ethanol and insolubilized. Without this process, the silk nanofiber can hardly be used as a nerve conduit since the silk nanofiber is weak against moisture. Later, the silk nanofiber may be separated from the collecting part by submerging the collecting part in the water. The separated silk nanofiber nerve conduit may be washed with distilled water additionally.

Hereinbelow, the present invention will be explained in greater detail with reference to examples and experimental examples. However, the examples are written only for illustrative purpose, and the present invention is not limited as the examples.

EXAMPLE 1

Producing Silk Nanofiber Nerve Conduit

Step 1: Preparing Fibrous Spinning Solution 40 g of dried cultivated cocoon was submerged in 1 L of mixed solution wherein 0.3% of sodium oleate and 0.2% (w/v) of sodium carbonate was dissolved, heated to boil for 1 hour, and washed repeatedly to remove sericin. The sericin-removed cocoon was dried again and dissolved in mixed solution at the ratio of 1/20 at 85° C. for 3 min, wherein the mixed solution included calcium chloride/water/ethanol at mole ratio of 1/8/2. This dissolved solution was placed in the dialyzing diaphragm (MWCO: 12-14 kDa) and underwent dialysis with distilled water for 3 days, and the silk fibroin solution having approximately 2% (w/w) concentration was obtained. After the solution was lyophilized, silk fibroin sponge which was appropriate for the secondary dissolution was prepared and perfectly dissolved in 13% concentration of the formic acid (over 98% purity); therefore, fibrous spinning solution was prepared.

Step 2: Preparing Silk Nanofiber Having Conduit-Shape

Electro-spinning was performed by the collecting part, which was the 1.65 mm of metallic rod coated with 10% of polyethileneoxide, wherein, the fibrous spinning solution produced in step 1 was electro-spun under the condition of 10 kV of applied voltage, 0.2 ml/time of releasing speed and 200 rpm of metallic rod spinning speed. When the diameter of collecting part to which the silk nanofiber was collected became 2.0 to 2.1 mm, the electro-spinning was ended, and the collected silk nanofiber was placed and dried in the atmosphere so that formic acid vaporized. Therefore, silk nanofiber having conduit-shape was prepared.

Step 3. Separation of Silk Nanofiber Having Conduit-Shape

The collecting part on which the silk nanofiber was integrated in conduit-shape from step 2 was submerged in ethanol for 1 hour and insolubilized, and submerged in water so that the silk nanofiber was separated from the collecting part. The separated silk nanofiber was washed with distilled water and a silk nanofiber nerve conduit was obtained.

EXPERIMENT EXAMPLE 1

Measurement of Structural Characteristics

The following experiment was performed in order to find out the structural characteristics of silk nanofiber nerve conduit of the present invention.

FIG. 1 presents photographic images of silk nanofiber nerve conduit of the Example 1. FIG. 2 presents electro-microscopic images of silk nanofiber nerve conduit regarding the present invention. For more details, (a) in FIG. 2 presents the cross-section of silk nanofiber nerve conduit, (b) and (c) of FIG. 2 present magnified cross section images, and (d) of FIG. 2 presents the fabric structure of the silk nanofiber nerve conduit surface.

According to FIG. 1, silk nanofiber nerve conduit of Example 1 of the present invention had circle-shaped cross section. The inside of the silk nanofiber nerve conduit was hollow and the thickness of the conduit was approximately 0.2 mm.

According to the (a),(b),(c) and (d) of FIG. 2, the cross section of silk nanofiber nerve conduit of Example 1 of the present invention had a structure in which fine fibers were stacked layer upon layer and silk nanofiber having a diameter of 200 to 400 nm were irregularly intertwined. Accordingly, silk nanofiber nerve conduit of Example 1 of the present invention had pores formed by the irregular intertwining of the fine fibers.

Accordingly, silk nanofiber nerve conduit of the present invention may exchange the body fluid in and out of conduit through the pores therein. This characteristic may solve the limitation caused by the absence of the existing pores in synthetic polymers nerve conduit wherein body fluid cannot be exchanged.

EXPERIMENT EXAMPLE 2

Measurement of Mechanical Property

The following experiment was performed in order to recognize the mechanical property of silk nanofiber nerve conduit of the present invention.

In order to test tensile strength of the nerve conduit, the conduit having 4 cm length was prepared. Inner diameter of the nerve conduit was 1.65 mm and the thickness of conduit wall was average 200 μm. Therefore, cross sectional area was 1.16 mm$^2$($[\{(1.65+0.4)/2\}^2-(1.65/2)^2]*\pi$). Tensile strength test was performed after submerging the conduit in normal saline solution for 1 hour. The ending of the sample which was swollen in the solution was fixed on test device. With 2 cm gauge length and 10 mm/min speed, the strength and elongation of severance was measured until desired position.

The result is as shown in Table 1 below.

TABLE 1

| | Example 1 |
|---|---|
| Cutting elongation (%) | 243 ± 15 |
| Cutting strength (MPa) | 4.92 ± 0.07 |
| Yield point (%) | 20 |

As referred in Table 1, elongation of severance was approximately 250%, the elongation at yield point was around 20% and maximum tensile strength was 4.92 MPa, which had sufficient tear strength to suture for surgical procedure. In this regard, the silk nanofiber nerve conduit of Example 1 of the present invention may be sufficient to connect severed nerve to nerve as a surgical suture. Therefore, silk nanofiber nerve conduit of the present invention may be used as a surgical suture.

EXPERIMENT EXAMPLE 3

Measurement of Nerve Regeneration Effect

The following experiment was performed in order to recognize the effect with respect to nerve regeneration of silk nanofiber nerve conduit of the present invention.

Three groups were set from randomly selected sample of rats, in which negative control group was prepared through the surgical procedure in which 8 mm length of ischiadic nerves from the middle of the femoral region of rat was cut and removed and followed by no treatment at all, positive control group was prepared through the surgical procedure in which 8 mm length of ischiadic nerves was cut from the middle and removed, the front and back sides of the nerves were switched and autografted to the rats, and experiment group was prepared through the surgical procedure in which 8 mm length of ischiadic nerves was cut from the middle and removed, and 10 mm length of silk nanofiber nerve conduit of Example 1 of the present invention was autografted to the nerve-removed area. After these groups were ready, ankle stance angel test (ASA) was performed at weeks 1, 4, 7, 10 (3 weeks interval) in order to test a motor skill of the mouse of each group.

After filming walking rats on the walking track at the side and under them with video camera, the film was analyzed through the image analyzing program. Also, in order to measure sensory function recovery, paw pressure test (PP) was performed, wherein upon covering the eyes of rat, the paws of the rat were placed under the sharp pressure tip of PP and with increments of pressure, the pressure was measured under which the rats had pain and cried. At this time, the subject showing freezing reaction due to phobia was excluded from the experiment. The result is as shown in Table 2 and FIG. 3.

<3-1> Ankle Stance Angle Test (ASA)

ASA indicates the extended angle in the middle of walking and the value is 90° for normal rats. The result is as shown as Table 2 below.

<3-2> Paw Pressure Test

PP indicates the moment under which the rats feel pain. As the pressure (g) is higher, sensory function decreases. The result is as shown as Table 2 below.

TABLE 2

|  |  | ASA (°) | PP (g) |
|---|---|---|---|
| Negative Control Group | Week 1 | 33 | 60.43 |
|  | Week 4 | 36 | 35.79 |
|  | Week 7 | 38 | 15.89 |
|  | Week 10 | 42 | 16.09 |
| Positive Control Group | Week 1 | 37 | 51.03 |
|  | Week 4 | 40 | 23.11 |
|  | Week 7 | 45 | 17.00 |
|  | Week 10 | 57 | 25.15 |
| Example 1 | Week 1 | 45 | 45.89 |
|  | Week 4 | 36 | 36.85 |
|  | Week 7 | 45 | 11.13 |
|  | Week 10 | 62 | 15.58 |

According to Table 2 and FIG. 3, as compared the result and 90° ASA value of normal rat, negative control group had 42° in week 10 (47% of normal rat), positive control group autografted autogenous nerve had 57° of improved function (63% of normal rat), and experiment group which was autografted silk nanofiber nerve conduit of Example 1 of the present invention had 62° (69% of normal rat) and showed the best improvement for a motor skill among the three groups. Therefore, it was observed that the experiment group had better improvement of motor skill than negative control group and excellent improvement of motor skill as compared to the positive control group.

Also, the measurement of week 10 of nerve injury, PP was resulted 16.09 g for negative control group, 25.15 g for positive control group autografted autogenous nerve, and 15.58 g for autografted silk nanofiber nerve conduit of Example 1 of the present invention. Regarding the recovery of sensory function, there was no significant difference between experiment group and other groups.

In clinic, recovery of motor skill is more important than that of sensory function; therefore, silk nanofiber nerve conduit of the present invention may be valuably used for nerve injury patients.

EXPERIMENT EXAMPLE 4

Measurement of Self-cleaving Indicator

Self-cleaving, one of the common symptoms of the injury of peripheral nerve, causes extreme pain as a result of forming neuroma. Therefore, observing the degree of self-cleaving may reflect the degree of pain which animal feels.

The following experiment was performed in order to find out the degree of pain in connection with nerve injury by autografting silk nanofiber nerve conduit of the present invention.

For the rats of three groups in experimental Example 3, the occurrence of self-cleaving was observed. Self-cleaving was recorded by each step. Step 1 was the self-cleaving at the level of claw, step 2 was the self-cleaving at the level of toe, step 3 was self-cleaving at the level of toe to sole and self-cleaving was at the level of more than sole over step 3. Since step 1 was perfectly recovered, more than step 2 which was impossibly recoverable step was regarded as serious condition. At this time, the subject showing extreme pain due to serious self-cleaving was excluded from the experiment.

The result is as shown in Table 3.

TABLE 3

| | Time after surgical procedure (week) | | | | | | | | | |
|---|---|---|---|---|---|---|---|---|---|---|
| | 1 | 2 | 3 | 4 | 5 | 6 | 7 | 8 | 9 | 10 |
| Incidence ratio of step 1(%): the self-cleaving of the claw level. | | | | | | | | | | |
| Negative control group | 0 | 20 | 80 | 60 | 60 | 60 | 60 | 60 | 60 | 60 |
| Positive control group | 50 | 50 | 50 | 50 | 50 | 50 | 50 | 75 | 75 | 75 |
| Example 1 | 0 | 0 | 0 | 17 | 33 | 33 | 50 | 67 | 83 | 83 |
| Incidence ratio of step 2(%): the self-cleaving of the toe level. | | | | | | | | | | |
| Negative control group | 0 | 0 | 60 | 60 | 60 | 60 | 60 | 60 | 60 | 60 |
| Positive control group | 0 | 25 | 25 | 25 | 50 | 50 | 50 | 50 | 50 | 50 |
| Example 1 | 0 | 0 | 0 | 0 | 0 | 17 | 33 | 50 | 50 | 50 |
| Incidence ratio of step 3(%): the self-cleaving of the toe to sole level. | | | | | | | | | | |
| Negative control group | 0 | 0 | 20 | 40 | 40 | 40 | 40 | 40 | 40 | 40 |
| Positive control group | 0 | 25 | 25 | 25 | 25 | 25 | 25 | 25 | 25 | 25 |
| Example 1 | 0 | 0 | 0 | 0 | 0 | 0 | 0 | 0 | 0 | 0 |
| Incidence ratio of step 3 among the whole self-cleaving incidents(%) | | | | | | | | | | |
| Negative control group | 0 | 0 | 25 | 67 | 67 | 67 | 67 | 67 | 67 | 67 |
| Positive control group | 0 | 33 | 33 | 33 | 33 | 33 | 33 | 33 | 33 | 33 |
| Example 1 | 0 | 0 | 0 | 0 | 0 | 0 | 0 | 0 | 0 | 0 |

According to the Table 3, for the negative control group having no treatment and positive control group autografted with autogenous nerve, self-cleaving was occurred within 1-2 weeks after surgical procedure. However, if silk nanofiber nerve conduit was autografted in Example 1 of the present invention, self-cleaving was occurred after 4 weeks from the surgical procedure. Also, according to the self-cleaving incidence ratio of step 2, the ratios of negative control group, positive control group and Example 1 were all similar to each other. According to the incidence ratio of more than step 3, negative control group indicated 67%, positive control group indicated 33% and Example 1 indicated 0% at 10 weeks after the surgical procedure. In this regard, if silk nanofiber nerve conduit was autografted for Example 1 of the present invention, self-cleaving incidence ratio was 0%. Therefore, the incidence rate of pain related to nerve disease which was followed by nerve injury was remarkably decreased even compared to the positive control group. Clinically, this result may be expected to reduce the pain of nerve disease which is the main complications of nerve injury as preventing chronic pain resulted from the sensory nerve recovery of practical patient.

EXPERIMENT EXAMPLE 5

Measuring Inside of Autografted Nerve Conduit

The following experiment was performed in order to recognize the inside feature of nerve conduit after autografting silk nanofiber nerve conduit of the present invention.

After 10 weeks from when rats were autografted silk nanofiber nerve conduit in Example 1 of Experimental Example 4, the inside of the conduit was scanned by a scanning electron microscope (SEM) and the result of the scanning was shown in (a) of FIG. 3. The result of scanning was magnified and shown in (b) of FIG. 3, and an arrow of (b) which indicates the cross-section of regenerated nerve bundle was magnified and shown in (c) of FIG. 3. The side of the regenerated nerve bundle which was marked by an arrow in (b) was shown in (d) of FIG. 3.

According to the (a) of FIG. 3, if silk nanofiber nerve conduit was autografted in Example 1 of the present invention, inside of the nerve conduit was filled. According to the (b) of FIG. 3 which was magnified inner view of the conduit, the material filled inside of nerve conduit was the gathering of fiber bundle composing fiber thread. According to (c) and (d) which was re-magnified (b) of FIG. 3, the fiber bundle was generated, gathering each fine fiber one by one with a uniform orientation. It is the essential characteristic of a normal nerve that each fiber is gathered into a small bundle, and the small bundles are gathered into a large bundle, and that the gathered fibres have uniform orientation. In this regard, when the silk nanofiber nerve conduit according to the present invention was autografted as discussed in Example 1, new axons with orientation were generated inside the autografted silk nanofiber nerve conduit.

Therefore, as new nerve tissue was generated inside the silk nanofiber nerve conduit of the present invention after nerve conduit was autografted, the silk nanofiber nerve conduit can be used to treat injured nerve.

EXPERIMENT EXAMPLE 6

Histological Measuring Inside of Autografted Nerve Conduit

The following experiment was performed in order to recognize cytological change of the ischiadic nerve and the degree of myelinated nerve when silk nanofiber nerve conduit of the present invention was autografted in injured ischiadic nerve.

After 10 weeks from when silk nanofiber nerve conduit was autografted to the rat in Example 1 of Experimental Example 4, ischiadic nerve sample was prepared as paraffin block and sliced 10 μm finely by microtome. Staining with Hematoxylin-Eosin stain (H&E) and Luxol fast blue stain (LFB) were carried out, respectively. After staining, the tissue was sealed for long term preservation. The images of the tissue were scanned by using OLYMPUS microscopy (BX-51 microscopy, Japan) and analyzed by image analyzer (KAPPA, USA). For H&E staining, after removing paraffin from the tissue, the tissue was stained in Hematoxylin solution for 10 min and Eosin solution for 1 min in order. For LFB staining, the tissue was placed in the luxol fast blue solution (95% ethanol including 0.1% of luxol fast blue MSBN and 0.05% of acetic acid) and reacted under 57° C. for 24 hours. After that, the tissue was washed with 95% alcohol and distilled water one by one and placed in 0.1% of cresyl violet solution under 37° C. for 1 hour in order to seperate the dying property of medulla and cortex of nerve cell. After staining, the tissue was sealed for safe preservation of tissue staining property. At that time, myelinated layer was stained blue and nerve cells were stained pink or purple. The result of H&E staining is shown (a) in FIG. 4, the result of LFB staining is shown (b) in FIG. 4, and the result of example 1 of (b) in FIG. 4 is magnified and shown in (c) of FIG. 4.

According to (a) of FIG. 4, for negative control group having no treatment, disconnected parts were presented on the slide image sliced 10 μm thickness since the regenerated nerves were spread as a radial shape without having directionality and various sizes of neuroma were generated in inconsistent place. For positive control group autografting autogenous nerve, autografted fragments were not spread from the middle without having directionality and held together in round shape toward the end wherein large mass of neuroma was formed. This was corresponding to the result of high self-cleaving (Table 3). Also, if silk nanofiber nerve conduit was autografted in Example 1 of the present invention, the mass filled inside of conduit where was empty was stained and it was recognized that the mass was cells having cytoplasm. According to (b) of FIG. 4, for negative and positive control group, nerve fibers were hold together where neuroma was placed. For autografting silk nanofiber nerve conduit in Example 1 of the present invention, the cells filled inside of the conduit were also stained blue and it was recognized that the cells were nerve cells having myelin sheath, which were myelinated cells. According to (c) of FIG. 4, nerve cells were regenerated from the growing direction of the blue-stained cell, i.e., from the middle to the end with directionality. In this regard, if silk nanofiber nerve conduit was autografted in Example 1, nerve cells were regenerated from the middle to the end with directionality.

Therefore, if silk nanofiber nerve conduit was autografted with regard to the present invention, as inside nerve tissue was regenerated from the middle to the end with directionality without generating neuroma, the silk nanofiber nerve conduit may be used to treat injured nerve.

Accordingly, the autograft of the silk nanofiber nerve conduit of the present invention has excellent biocompatibility; allows the body fluid to be exchanged in and out of conduit through pores of the conduit; and has a proper elasticity, tensile strength, and tear strength. Due to these properties, the silk nanofiber nerve conduit of the present invention helps the regeneration of the nerve injury to recover a motor skill and a sensory function, and shows an excellent effect of nerve regeneration. Therefore, the silk nanofiber nerve conduit of the present invention may be used in treating a nerve injury as a replacement of an existing synthetic polymeric nerve conduit. Also, it is expected that the incidence of pain associated with nerve disease which is defined as an important complication of nerve injury may be minimized.

The invention claimed is:
1. A method for producing silk nanofiber nerve conduit, the method comprising:
    preparing fibrous spinning solution (Step 1); the preparing comprising:
        removing of sericin from silk fiber (Step a);
        preparing silk fibroin solution by washing, drying and dialyzing sericin-removed silk fiber (Step b);
        preparing silk fibroin sponge by lyophilizing the silk fibroin solution (Step c); and
        dissolving the silk fibroin sponge with designated solvent and filtering the product (Step d);
    producing a silk nanofiber having a diameter of 200-400 nm and stacked layer-upon-layer to form a porous conduit shape having a thickness of 0.1-0.3 mm by electrospinning at 100-300 rpm the fibrous spinning solution prepared in step 1 into a cylindrical collecting part coated with polyethyleneoxide (PEO) (Step 2) until an outer diameter of the porous conduit shape is 2.0 to 2.1 mm; and
    submerging the collecting part in methanol or ethanol to insolubilize the silk nanofiber; submerging in water for separation and separating the silk nanofiber of conduit-shape produced in step 2 from the collecting part, thereby forming the silk nanofiber nerve conduit, wherein the outer diameter of the collected silk nanofiber nerve conduit is 2.0-2.1 mm and the size of the pores formed on the silk nanofiber nerve conduit is between 50 and 250 μm (Step 3).
2. A method for producing silk nanofiber conduit according to claim 1, wherein the fibrous spinning solution is prepared at 12 to 18% of concentration.

3. A method of producing silk nanofiber conduit according to claim 1, wherein the cylindrical collecting part coated with polyethyleneoxide of step 2 is a metallic rod coated with 5 to 15% of polyethyleneoxide.

4. A method of producing silk nanofiber conduit according to claim 1, wherein 5 to 20 kV of voltage range is applied in the electro-spinning of step 2.

* * * * *